United States Patent
Develter (10) Patent No.: US 11,696,585 B2
(45) Date of Patent: Jul. 11, 2023

(54) BAKERY COMPOSITION

(71) Applicant: PURATOS NV, Groot-Bijgaarden (BE)

(72) Inventor: Bram Develter, Kampenhout (BE)

(73) Assignee: PURATOS NV, Groot-Bijgaarden (BE)

( * ) Notice: Subject to any disclaimer, the term of this patent is extended or adjusted under 35 U.S.C. 154(b) by 880 days.

(21) Appl. No.: 16/312,710

(22) PCT Filed: Jul. 10, 2017

(86) PCT No.: PCT/EP2017/067211
§ 371 (c)(1),
(2) Date: Dec. 21, 2018

(87) PCT Pub. No.: WO2018/011117
PCT Pub. Date: Jan. 18, 2018

(65) Prior Publication Data
US 2019/0208794 A1    Jul. 11, 2019

(30) Foreign Application Priority Data

Jul. 11, 2016 (BE) .................. 2016/5579

(51) Int. Cl.
*A21D 8/04* (2006.01)
*A21D 2/26* (2006.01)
*C12N 9/00* (2006.01)
*C12N 9/50* (2006.01)

(52) U.S. Cl.
CPC ............ *A21D 8/042* (2013.01); *A21D 2/26* (2013.01); *A21D 8/04* (2013.01); *C12N 9/00* (2013.01); *C12N 9/50* (2013.01); *C12Y 301/01003* (2013.01); *C12Y 304/21111* (2013.01)

(58) Field of Classification Search
None
See application file for complete search history.

(56) References Cited

U.S. PATENT DOCUMENTS

| | | | |
|---|---|---|---|
| 3,368,903 A | 2/1968 | Johnson et al. | |
| 6,923,994 B2 * | 8/2005 | Sturkenboom | A21D 8/042 426/549 |
| 2005/0255204 A1 | 11/2005 | Arnaut et al. | |
| 2007/0190552 A1 | 8/2007 | Saul et al. | |
| 2011/0097440 A1 * | 4/2011 | Van Winckel | A21D 13/80 426/20 |
| 2013/0323359 A1 * | 12/2013 | Budolfsen | C11B 3/003 426/20 |
| 2015/0140168 A1 | 5/2015 | Bellido et al. | |

FOREIGN PATENT DOCUMENTS

| | | |
|---|---|---|
| EP | 0776604 A1 | 6/1997 |
| EP | 1982597 A1 | 10/2008 |
| JP | 45-11547 B | 4/1970 |
| RU | 2140740 C1 | 11/1999 |
| RU | 2338378 C2 | 11/2008 |
| WO | WO-9404035 A1 * 3/1994 ............ A21D 8/042 |
| WO | 2009/138447 A1 | 11/2009 |
| WO | WO 2009/138447 A1 | 11/2009 |
| WO | 2018/011117 A1 | 1/2018 |

OTHER PUBLICATIONS

International Search Report and Written Opinion for PCT International Patent Application No. PCT/EP2017/067211, dated Aug. 31, 2017.
International Search Report and Written Opinion for International Application No. PCT/EP2017/067211, dated Aug. 31, 2018 (9 pages).
International Preliminary Report on Patentability for PCT/EP2017/067211, dated Jan. 15, 2019 (7 pages).
Stoytcheva et al. (2012) "Analytical Methods for Lipases Activity Determination: A Review," Current Analytical Chemistry, 8:400-407.
Van Oort, "Enzymes in Bread Making", Enzymes in Food Technology, $2^{nd}$ Edition, 2010, Chapter 6, pp. 103-143.
Dictionary of Biochemistry, $3^{rd}$ Edition, 1988, pp. 1481-1482.
ExPASy ENZYME entry: EC 3.1.1.3[online], Jun. 15, 2016, [Retrieved May 11, 2022], URL:https://web.archive.org/web/20160615150952/http://enzyme.expasy.org/EC/3.1.1.3.
ExPASy ENZYME entry: EC 3.1.1.23[online], Mar. 4, 2016, [Retrieved May 11, 2022], URL:https://web.archive.org/web/20160304065646/http://enzyme.expasy.org/EC/3.1.1.23.
ExPASy ENZYME entry: EC 3.1.1.26[online], Mar. 4, 2016, [Retrieved May 11, 2022], URL:https://web.archive.org/web/20160304065907/http://enzyme.expasy.org/EC/3.1.1.26.
ExPASy ENZYME entry: EC 3.1.1.78[online], Mar. 3, 2016 [Retrieved May 11, 2022], URL:https://web.archive.org/web/20160303215136/http://enzyme.expasy.org/EC/3.1.1.78.
ExPASy ENZYME entry: EC 3.1.1.4[online], Mar. 3, 2016 [Retrieved May 11, 2022], URL:https://web.archive.org/web/20160303212033/http://enzyme.expasy.org/EC/3.1.1.4.

* cited by examiner

*Primary Examiner* — Jenna A Watts
(74) *Attorney, Agent, or Firm* — Lathrop GPM LLP; James H. Velema; Judith L. Stone-Hulslander (57) ABSTRACT

It has been found that the combination of enzymes, in particular the combination of a thermophilic serine protease and a lipase, are able to improve the short bite in bakery products. Provided herein are compositions comprising these enzymes, the use of this combination of enzymes and methods for preparing bakery products using the combination of a thermophilic serine protease and a lipase.

20 Claims, 2 Drawing Sheets

BAKERY COMPOSITION

CROSS-REFERENCE TO RELATED APPLICATIONS

This application is a 35 U.S.C. § 371 filing of International Patent Application No. PCT/EP2017/067211, filed Jul. 10, 2017, which claims priority to Belgium Patent Application No. 2016/5579, filed Jul. 11, 2016, the entire contents of which are incorporated herein by reference.

FIELD OF THE INVENTION

The present invention relates to the improvement of the short bite of bakery products.

BACKGROUND OF THE INVENTION

When buying bakery products consumers take into account a series of parameters such as appearance, softness, moistness or aroma. The way the bakery product can be eaten is also imperative, the bakery product should for instance be easily bitten without having to chew it extensively, because this particular aspect is considered to be a characteristic of the freshness of the product. Consumers also prefer to buy breads with the lowest possible (labelled) additives.

During staling, the characteristics of a bakery product change. In particular, the aroma profile changes, the product becomes harder, dryer and it becomes more difficult to chew, and as a result the bakery product is considered to become "less fresh".

The short bite of a bakery product can be defined as the easiness to bite into or to tear off a piece of the bakery product. It is reflected by the force needed to break a sample and the number of chews to masticate a sample to a consistency ready for swallowing. In a way, the short bite is the opposite of the chewiness. Furthermore short bite is very different from softness. Indeed softness of a bread is reflected by the force needed to compress a sample till a certain deformation. Softness is also the opposite of hardness. A bread can therefore be soft while having no short bite and vice versa.

Currently there have already been some methods proposed to improve the short bite of a bakery product. EP0776604 describes the use of unsaturated monoglycerides to produce microwavable crispy bread-roll having short bite. WO2009138447 describes the use of an intermediate thermostable or thermostable serine or metallo-protease to improve the short bite of bakery products.

However it has been observed that these methods have their limitations. In Europe, the addition of monoglycerides or other emulsifiers requires specific labelling of the bakery products with an E-number, something which prevents some consumers from buying the product.

The use of an intermediate thermostable or a thermostable serine or metallo-protease improves the short bite of bakery products to a certain extent, but this improvement of short bite is somehow limited as high amounts of enzyme tend to be detrimental to other bakery product properties, such as the crumbliness and the resiliency.

There is therefore a need for new methods and products to further improve the short bite.

SUMMARY OF THE INVENTION

The inventors have found that the use of combination of a thermophilic serine protease having an optimum activity at a temperature higher than 70° C. and a lipase in bakery applications, and in particular in bread making, has a synergistic effect on short bite.

Accordingly, in a first aspect, the present invention relates to a composition comprising:
- at least one first enzyme, wherein said first enzyme is a thermophilic serine protease having an optimum activity at a temperature higher than 70° C., preferably at a temperature higher than 80° C.; and;
- at least one second enzyme, wherein said second enzyme is a lipase.

In a particular embodiment the composition as disclosed herein provides that said first enzyme is a thermophilic serine protease wherein the ratio between the protease activity at optimum temperature and the protease activity at 25° C. is higher than 10, preferably higher than 15.

In a particular embodiment the composition as disclosed herein provides that said first enzyme is a neutral or an alkaline thermophilic serine protease.

In a particular embodiment the composition as disclosed herein provides that said first enzyme is a Taq protease, preferably isolated from *Thermus aquaticus*, preferably aqualysin I or aqualysin II, more preferably aqualysin I, even more preferably aqualysin I isolated from *Thermus aquaticus* LMG8924.

In a particular embodiment the composition as disclosed herein provides that said first enzyme is present in an amount of 100 to 1200 units/100 kg of flour, preferably at 200 to 900 units/100 kg of flour, more preferably at 350 to 700 units/100 kg of flour.

In a particular embodiment the composition as disclosed herein provides that said second enzyme is a triacylglycerol lipase or triacylglycerol acylhydrolase as defined by enzyme entry EC 3.1.1.3, preferably selected from lipases obtained from *Thermomyces lanuginosus*, *Rhizopus oryzae* and *Rhizomucor miehei*.

In a particular embodiment the composition as disclosed herein provides that said second enzyme is present in an amount of 5 to 100 LU/100 kg of flour of lipase from *Thermomyces lanuginosus*; at 0.023 to 0.360 LU/100 kg of flour of lipase from *Rhizopus oryzae*; and at 50 to 200 LU/100 kg of flour of lipase from *Rhizomucor miehei*.

Accordingly, in a further aspect, the present invention relates to the use of a composition as disclosed herein in bakery applications.

In a particular embodiment the composition as disclosed herein is used in bread improvers.

In a particular embodiment the composition as disclosed herein is used in soft bakery products and crusty bakery products, preferably bread, soft rolls, donuts, buns, microwavable buns, Danish pastry, croissants, hamburger rolls, pizza and pita bread and cake.

Accordingly, in a further aspect, the present invention relates to a bread improver comprising the composition as disclosed herein.

Accordingly, in a further aspect, the present invention relates to a method for preparing a baked product, comprising the steps of adding to the dough or batter, prior to baking:
- at least one first enzyme, wherein said first enzyme is a thermophilic serine protease having an optimum activity at a temperature higher than 70° C., preferably at a temperature higher than 80° C.; and;
- at least one second enzyme, wherein said second enzyme is a lipase.

In a particular embodiment the method as disclosed herein provides that said baked product shows improved short bite, preferably wherein the maximum force needed to break a baked product, prepared using at least one first enzyme being a thermophilic serine protease having an optimum activity at a temperature higher than 70° C., preferably at a temperature higher than 80° C., and using at least one second enzyme being a lipase; is reduced with at least 15% compared to a reference baked product prepared using none of said first or second enzyme.

Accordingly, in a particular embodiment, the composition as disclosed herein is used in the preparation of a baked product with an improved short bite, wherein, preferably, the maximum force needed to break the prepared baked product is reduced with at least 15% compared to a reference baked product prepared using none of said first or second enzyme.

In a particular embodiment the method as disclosed herein provides that no adverse effects on dough rheology, on the crumb structure and on the volume of the resulting bakery product are observed.

Accordingly, in a further aspect, the present invention relates to a baked product prepared from a dough or batter comprising the composition as disclosed herein.

BRIEF DESCRIPTION OF THE FIGURES

FIG. 1 (A to C) represents different aspects of the evaluation of the short bite with the aid of a texture analyser.

DETAILED DESCRIPTION

Before the present products, compositions, uses and methods of the invention are described, it is to be understood that this invention is not limited to particular products, compositions, uses and methods or combinations described, since such products, compositions, uses and methods and combinations may, of course, vary. It is also to be understood that the terminology used herein is not intended to be limiting, since the scope of the present invention will be limited only by the appended claims.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. It will be appreciated that the terms "comprising", "comprises" and "comprised of" as used herein comprise the terms "consisting of", "consists" and "consists of".

The recitation of numerical ranges by endpoints includes all numbers and fractions subsumed within the respective ranges, as well as the recited endpoints.

The term "about" or "approximately" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform the disclosed invention. It is to be understood that the value to which the modifier "about" or "approximately" refers is itself also specifically, and preferably, disclosed.

Whereas the terms "one or more" or "at least one", such as one or more or at least one member(s) of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members.

All references cited in the present specification are hereby incorporated by reference in their entirety. In particular, the teachings of all references herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

The inventors have surprisingly found that by using a new combination of enzymes, in particular the combination of a thermophilic serine protease and a lipase, it was possible to obtain an improvement of the short bite that was by far more significant compared to the short bite improvement expected for the addition of the enzymes when used alone.

Figure 1A:
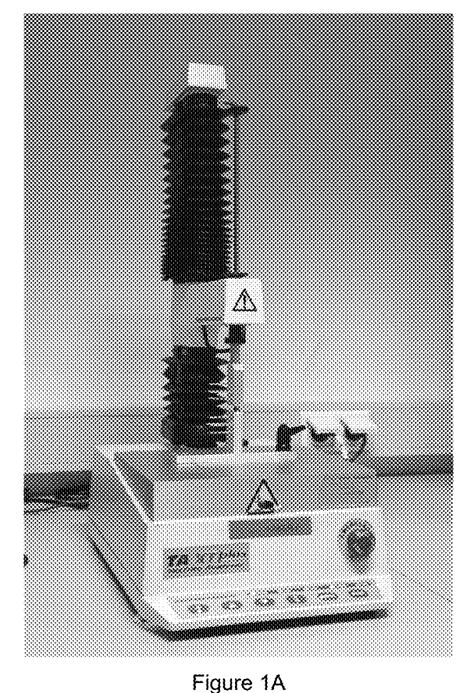
FIG. 1A represents a texture analyser equipped with a pizza tensile rig (2 probes with pins.
Figure 1B:
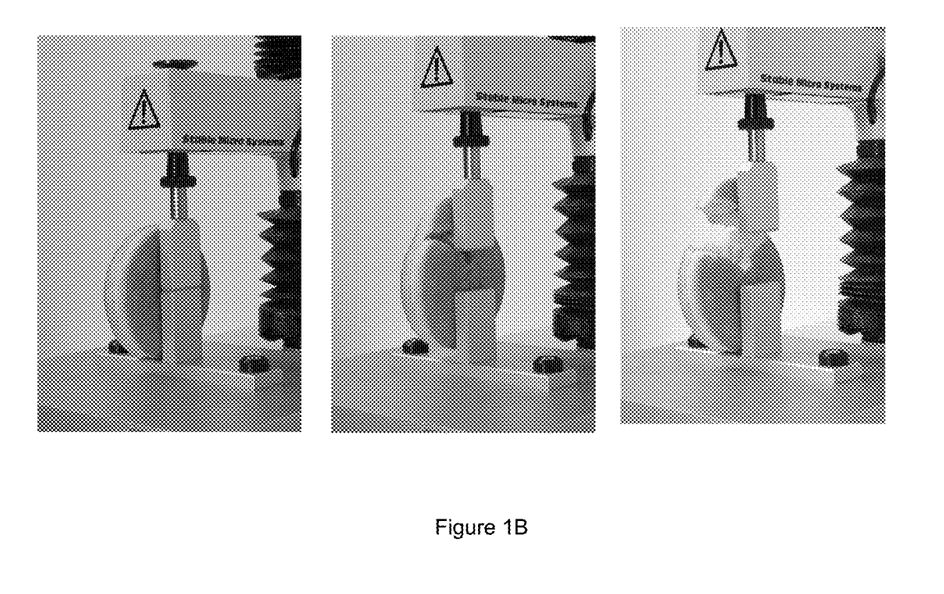
FIG. 1B represents the actual measurement setup, wherein a bun is attached to the pizza tensile rig and wherein the upper probe is moved up at a constant speed until the bun breaks.
Figure 1C:
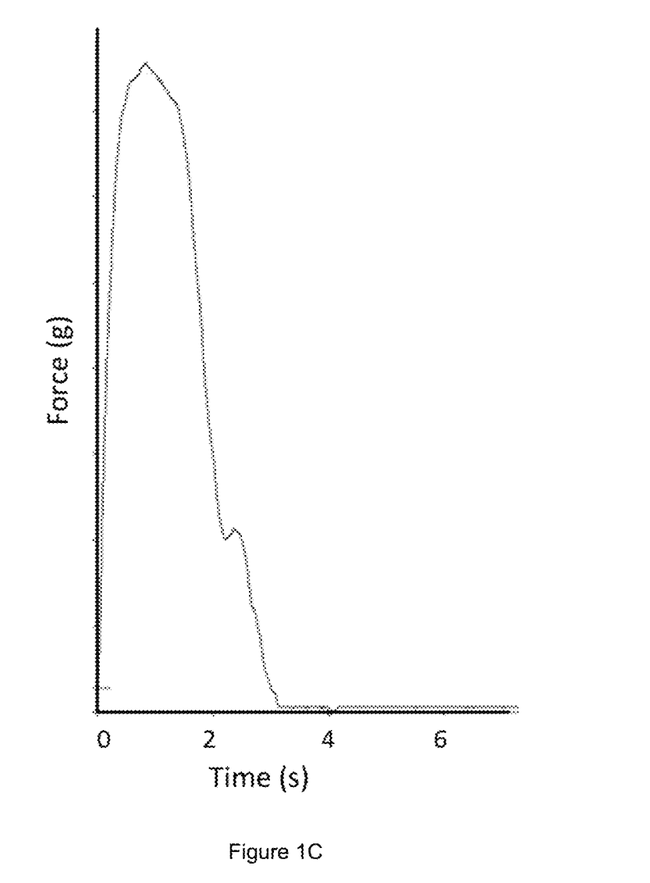
FIG. 1C shows a typical graph of the measurement wherein the needed force expressed in gram (g) is measured in function of time (s).

Short bite, also sometimes referred to as opposite to chewiness and/or to toughness, is used to designate the force needed to break a sample of a bakery product and/or the number of chews needed to masticate a bakery product sample until a consistency that makes it ready to swallow. Short bite can be easily measured by a trained taste panel of people and can be reasonably quantified using an arbitrary short bite scale. Such techniques are well known in the food industry and are generally referred to as organoleptic testing. In such a method, an initial training session is organized to familiarize the panellists with the range of products that will be tested. In this session, reference standards are presented to train the panellists to recognize the differences between the product attributes that are to be measured. In a second step, the panellists receive a number or products they have to score on short bite, on a scale from 0 to 10. Short bite may also be evaluated with the aid of a texture analyser. In such a method, a bun is attached to a pizza tensile rig (2 probes with pins (see FIG. 1A)). The upper probe will move up at a constant speed and in this way break the bun (see FIG. 1B). The needed force expressed in gram (g) is measured by the texture analyser. Throughout this process, the required force will increase until the bun breaks and the force decreases. A typical graph of this measurement in shown in FIG. 1C. The maximum force ($F_{max}$) measured is a common parameter for evaluating short bite.

The inventors have surprisingly found that the simultaneous use of a sufficient amount of a thermophilic serine protease and a sufficient amount of a lipase in a dough before baking shows an unexpected synergistic effect on the improvement of the short bite in the baked product.

Indeed the short bite given by the combination of the two types of enzymes is bigger than the sum of the effects of the enzymes taken individually. There is a synergy when the effect given by amount x of the thermophilic serine protease combined with amount y of the lipase is bigger than the sum of the effect given by amount x of the thermophilic serine protease and the effect given by the amount y of the lipase.

Accordingly, in a first aspect, the present invention relates to a composition comprising:
- at least one first enzyme, wherein said first enzyme is a thermophilic serine protease; and;
- at least one second enzyme, wherein said second enzyme is a lipase.

In a particular embodiment said first enzyme is a thermophilic serine protease having an optimum activity at a temperature higher than 70° C., preferably at a temperature higher than 75° C. and more preferably at a temperature higher than 80° C.

It has further been found that the synergistic effect that is referred to herein is particularly present when the thermophilic serine protease as referred to herein has an optimum activity at a temperature higher than 70° C., preferably at a temperature higher than 75° C. and more preferably at a temperature higher than 80° C.

As used herein, the term "protease" refers generally to enzymes (also referred to as peptidases or proteinases) that hydrolyse the peptide bonds that link amino acids together in a polypeptide chain preferably as defined by enzyme entry EC 3.4. They are classified in several classes according to their catalytic residues. Among these classes, serine proteases (or serine endopeptidases) are proteases that cleave peptide bonds in proteins, in which serine serves as the nucleophilic amino acid at the active site. Serine proteases are defined by enzyme entry EC 3.4.21. Serine proteases may be further sub classified according to their substrate specificity as trypsin-like, chymotrypsin-like, thrombin-like, elastase-like or subtilisin like.

In the context of the present invention the protease activity is measured using azurine crosslinked casein (AZCL-casein) as a substrate. Hydrolysis by proteases produces water soluble dyed fragments, and the rate of release of these (e.g. increase in absorbance at 590 nm) can be related directly to enzyme activity (Protazyme AK Tablets, Megazyme, Ireland). More details on the protease activity measurement are given in the examples. The protease activity can also be measured with other assays for protease activity known by persons skilled in the art. Among these is the calorimetric method using casein as substrate followed by the detection of the released amino acids with the Folin & Ciocalteu's Phenol reagent.

As used herein, the term "thermophilic" and in particular "thermophilic protease" as used herein, refers to proteases active at elevated temperatures. In particular the thermophilic protease(s) has an activity optimum at a temperature higher than 70° C., preferably at a temperature higher than 75° C. and more preferably at a temperature higher than 80° C.

As used herein, the term "lipase" refers generally to triacylglycerol lipases or triacylglycerol acylhydrolase as defined by enzyme entry EC 3.1.1.3. Lipases are defined herein as enzymes that catalyze the hydrolysis of triacylglycerols to give free fatty acids, diacylglycerols, monoacylglycerols and glycerol. The lipase used in the compositions defined herein may comprise enzymatic side-activities such as for example phospholipase activity.

In the context of the present invention the lipase activity is measured using p-nitrophenyl palmitate (pNPP) as substrate and according to the method described herein. The enzyme activity can also be measured with other assays for lipase activity known by persons skilled in the art (for a review see for example Stoytcheva M. & al, 2012, Current Analytical Chemistry, vol 8, p. 400).

In particular, the lipase activity is measured using p-nitrophenyl palmitate (pNPP) as substrate. The release of yellow p-nitrophenol due to hydrolysis of p-nitrophenyl palmitate by lipase is measured by spectrophotometry at 414 nm. One lipase milliunit (LmU) is defined as the amount of enzyme needed to release one nanomole (nmole) per minute of p-nitrophenol from p-nitrophenyl palmitate at 45° C. and pH 7.5. More details on the lipase activity measurement are given in the examples. The enzyme activity can also be measured with other assays for lipase activity known by persons skilled in the art (for a review see for example Stoytcheva M. & al, 2012, Current Analytical Chemistry, vol 8, p. 400).

In a particular embodiment the composition as disclosed herein provides that said first enzyme is a thermophilic serine protease wherein the ratio between the protease activity at optimum temperature and the protease activity at 25° C. is higher than 10, preferably higher than 15. By providing that said ratio is higher than 10, the thermophilic serine protease as used herein provides that improved effects on short bite are obtained.

In a particular embodiment the composition as disclosed herein provides that said first enzyme is obtained by extraction from naturally-occurring eukaryotic or prokaryotic organisms, by synthesis or by genetic engineering. In a particular embodiment the composition as disclosed herein provides that said first enzyme is a neutral or an alkaline thermophilic serine protease. While fungal proteases are sensitive to high temperatures, bacterial neutral and alkaline proteases are more resistant to higher heat treatments.

In a particular embodiment the composition as disclosed herein provides that said first enzyme is a Taq protease, preferably isolated from *Thermus aquaticus*, preferably aqualysin I or aqualysin II, more preferably aqualysin I, and even more preferably aqualysin I isolated from *Thermus aquaticus* LMG8924.

In a particular embodiment the composition as disclosed herein provides that said first enzyme, preferably aqualysin I, is present in an amount of 100 to 1200 units/100 kg of flour, preferably at 200 to 900 units/100 kg of flour, more preferably at 350 to 700 units/100 kg of flour. Aqualysin I is advantageously added to the dough/batter at 100 to 1200 units/100 kg of flour, preferably at 200 to 900 units/100 kg of flour, more preferably at 350 to 700 units/100 kg of flour, the enzyme activity being obtained using the method described herein.

In a particular embodiment the composition as disclosed herein provides that said second enzyme is a triacylglycerol lipases or triacylglycerol acylhydrolase as defined by enzyme entry EC 3.1.1.3, preferably selected from lipases obtained from *Thermomyces lanuginosus, Rhizopus oryzae* and *Rhizomucor miehei*.

In a particular embodiment the composition as disclosed herein provides that said second enzyme is present in an amount of 5 to 100 LU, preferably at 15 to 75 LU, more preferably 20 to 60 LU/100 kg of flour of lipase from *Thermomyces lanuginosus*; at 0.023 to 0.360 LU, preferably at 0.09 to 0.18 LU/100 kg of flour of lipase from *Rhizopus oryzae*; and at 50 to 200 LU, preferably 90 to 160 LU, more preferably at about 138 LU/100 kg of flour of lipase from *Rhizomucor miehei*, the enzyme activity being obtained using the method described herein.

In a particular embodiment the composition as disclosed herein provides that the ratio of the amounts of units of said first enzyme versus the amounts of units of said second enzyme ranges between 5 and 35 (for Taq protease and the lipase from *Thermomyces lanuginosus*), between 1950 and 7800 (for Taq protease and the lipase from *Rhizopus oryzae*) and/or between 2 and 8 (for Taq protease and the lipase from *Rhizomucor miehei*).

In a particular embodiment the composition as disclosed herein is a bread improver, a patisserie mix or a patisserie premix, preferably a bread improver.

"Bread improvers" (also referred to as "dough conditioners", "dough improvers" or "improving agent" or "flour treatment agent") are typically added to the dough during baking in order to improve texture, volume, flavour and freshness of the baked product as well as to improve machinability and stability of the dough. Typically, a bread improver comprises or consists of: one or more enzymes (such as e.g. amylases, xylanases, phospholipases, oxidases, lipoxygenases, dehydrogenases and laccases), one or more oxidizing or reducing agents (such as e.g. ascorbic acid, glutathione, cysteine), one or more emulsifiers (such as e.g. monoglycerides (or mixtures of monoglycerides and diglycerides), monoglycerides derivatives (as for example succinylated lactylated or acetylated monoglycerides, diacetyl tartaric acid esters of monoglycerides (DATEM), glycerol monostearate (GMS), propylene glycol monoester, . . . ), sorbitan emulsifiers (sorbitan monostarate), polysorbates, sodium stearoyl lactylate (SSL), polyglycerol esters, sucrose esters and lecithin), one or more lipid materials (such as e.g. margarine, butter, oil, shortening), one or more vitamins (such as e.g. pantothenic acid and vitamin E), one or more gums, and/or one or more sources of fibre (such as e.g. oat fibre). Patisserie mixes typically comprise all the ingredients of a patisserie product recipe with the exception of water, fat (oil, butter, margarine) and eggs. Patisserie premixes are typically patisserie mixes where all or part of the flour and sugar has been removed.

In a particular embodiment the composition as disclosed herein is a dough or batter comprising flour and at least one first enzyme, wherein said first enzyme is a thermophilic serine protease preferably having an optimum activity at a temperature higher than 70° C., preferably at a temperature higher than 75° C. and more preferably at a temperature higher than 80° C.; and; at least one second enzyme, wherein said second enzyme is a lipase.

In particular, said second enzyme is present in an amount of 5 to 100 LU, preferably at 15 to 75 LU, more preferably 20 to 60 LU/100 kg of flour of lipase from *Thermomyces lanuginosus*; at 0.023 to 0.360 LU, preferably at 0.09 to 0.18 LU/100 kg of flour of lipase from *Rhizopus oryzae*; and at 50 to 200 LU, preferably 90 to 160 LU, more preferably at about 138 LU/100 kg of flour of lipase from *Rhizomucor miehei*, the enzyme activity being obtained using the method described herein.

In a further embodiment the composition as disclosed herein may further comprise appropriate amounts of one or more enzymes (such as e.g. amylases, xylanases, phospholipases, oxidases, lipoxygenases, dehydrogenases and laccases), one or more oxidizing or reducing agents (such as e.g. ascorbic acid, glutathione, cysteine), one or more emulsifiers (such as e.g. monoglycerides (or mixtures of monoglycerides and diglycerides), monoglycerides derivatives (as for example succinylated lactylated or acetylated monoglycerides, diacetyl tartaric acid esters of monoglycerides (DATEM), glycerol monostearate (GMS), propylene glycol monoester, . . . ), sorbitan emulsifiers (sorbitan monostarate), polysorbates, sodium stearoyl lactylate (SSL), polyglycerol esters, sucrose esters and lecithin), one or more lipid materials (such as e.g. margarine, butter, oil, shortening), one or more vitamins (such as e.g. pantothenic acid and vitamin E), one or more gums, and/or one or more sources of fibre (such as e.g. oat fibre).

In a further embodiment the composition as disclosed herein comprises:
  at least one first enzyme, wherein said first enzyme is a thermophilic serine protease preferably having an optimum activity at a temperature higher than 70° C., preferably at a temperature higher than 75° C. and more preferably at a temperature higher than 80° C.;
  one or more monoglycerides; and;
  at least one second enzyme, wherein said second enzyme is a lipase.

As used herein, the term "monoglycerides" refers generally to a class of glycerides which are composed of a molecule of glycerol linked to a fatty acid via an ester bond.

Monoglycerides are one of the many types of emulsifiers used in bakery applications: among these are monoglycerides (or mixtures of monoglycerides and diglycerides; referred as E471 by the International Numbering System for Food Additives (INS) or as 184.1505 by the US Food and Drug Agency), monoglycerides derivatives (as for example succinylated lactylated or acetylated monoglycerides, diacetyl tartaric acid esters of monoglycerides (DATEM), glycerol monostearate (GMS), propylene glycol monoester, . . . ), sorbitan emulsifiers (sorbitan monostarate), polysorbates, sodium stearoyl lactylate (SSL), polyglycerol esters, sucrose esters and lecithin.

Furthermore, in a further aspect, the present invention relates to the use of a composition as disclosed herein in bakery applications. In the context of the present invention, bakery applications refer to applications related to both bread and patisserie products. In particular said bakery products are soft bakery products and/or crusty bakery products, preferably bread, soft rolls, donuts, buns, microwavable buns, Danish pastry, croissants, hamburger rolls, pizza and pita bread and cake.

In a particular embodiment the use of the composition as disclosed herein in bread improvers, in patisserie mixes or in patisserie premixes is provided.

It is therefore an object of the present invention to provide in the use of the compositions according to the present invention to improve the short bite of bakery products which comprise the step of adding to the dough before baking a sufficient amount of one or more thermophilic serine protease(s) and a sufficient amount of one or more lipase(s) as disclosed herein.

In a particular embodiment the composition as disclosed herein is used for the improvement of short bite in baked products.

In a further aspect, disclosed herein is a method for preparing a baked product, comprising the steps of adding to the dough or batter, prior to baking:
- at least one first enzyme, wherein said first enzyme is a thermophilic serine protease; and;
- at least one second enzyme, wherein said second enzyme is a lipase.

In particular said first enzyme is a thermophilic serine protease having an optimum activity at a temperature higher than 70° C., preferably at a temperature higher than 75° C. and preferably at a temperature higher than 80° C.

In the context of the present invention the protease activity is measured using azurine crosslinked casein (AZCL-casein) as a substrate. Hydrolysis by proteases produces water soluble dyed fragments, and the rate of release of these (e.g. increase in absorbance at 590 nm) can be related directly to enzyme activity (Protazyme AK Tablets, Megazyme, Ireland). More details on the protease activity measurement are given in the examples. The protease activity can also be measured with other assays for protease activity known by persons skilled in the art. Among these is the calorimetric method using casein as substrate followed by the detection of the released amino acids with the Folin & Ciocalteu's Phenol reagent.

In the context of the present invention the lipase activity is measured using p-nitrophenyl palmitate (pNPP) as substrate and according to the method described herein. The enzyme activity can also be measured with other assays for lipase activity known by persons skilled in the art (for a review see for example Stoytcheva M. & al, 2012, Current Analytical Chemistry, vol 8, p. 400).

In a particular embodiment the method as disclosed herein provides that said first enzyme is a thermophilic serine protease wherein the ratio between the protease activity at optimum temperature and the protease activity at 25° C. is higher than 10, preferably higher than 15. By providing that said ratio is higher than 10, the thermophilic serine protease as used herein provides that improved effects on short bite are obtained.

In a particular embodiment the method as disclosed herein provides that said first enzyme is obtained by extraction from naturally-occurring eukaryotic or prokaryotic organisms, by synthesis or by genetic engineering. In a particular embodiment the composition as disclosed herein provides that said first enzyme is a neutral or an alkaline thermophilic serine protease.

In a particular embodiment the method as disclosed herein provides that said first enzyme is a Taq protease, preferably isolated from *Thermus aquaticus*, preferably aqualysin I or aqualysin II, more preferably aqualysin I, and even more preferably aqualysin I isolated from *Thermus aquaticus* LMG8924.

In a particular embodiment in the method as disclosed herein said first enzyme, preferably aqualysin I, is added to the dough or batter in an amount of 100 to 1200 units/100 kg of flour, preferably at 200 to 900 units/100 kg of flour, more preferably at 350 to 700 units/100 kg of flour. Aqualysin I is advantageously added to the dough/batter at 100 to 1200 units/100 kg of flour, preferably at 200 to 900 units/100 kg of flour, more preferably at 350 to 700 units/100 kg of flour, the enzyme activity being obtained using the method described herein.

In a particular embodiment the method as disclosed herein provides that said second enzyme is a triacylglycerol lipases or triacylglycerol acylhydrolase as defined by enzyme entry EC 3.1.1.3, preferably selected from lipases obtained from *Thermomyces lanuginosus, Rhizopus oryzae* and *Rhizomucor miehei*.

In a particular embodiment the method as disclosed herein provides that said second enzyme is added to the dough or batter in an amount of 5 to 100 U, preferably at 15 to 75 U, more preferably 20 to 60 U/100 kg of flour of lipase from *Thermomyces lanuginosus*; at 0.023 to 0.360 U, preferably at 0.09 to 0.18 U/100 kg of flour of lipase from *Rhizopus oryzae*; and at 50 to 200 U, preferably 90 to 160 U, more preferably at about 138 U/100 kg of flour of lipase from *Rhizomucor miehei*, the enzyme activity being obtained using the method described herein.

In a particular embodiment of the method as disclosed herein appropriate amounts of enzymes may be added directly to the dough or the batter during its preparation or before mixing of the ingredients. In other embodiments the enzymes may be added as part of an (bread) improver, a patisserie mix or premix, preferably as part of a bread improver. In particular the enzymes or the bread improver are added before proofing.

In a particular embodiment is disclosed herein is a method for preparing a baked product, comprising the steps of adding to the dough or batter, prior to baking:
- at least one first enzyme, wherein said first enzyme is a thermophilic serine protease preferably having an optimum activity at a temperature higher than 70° C., preferably at a temperature higher than 75° C. and more preferably at a temperature higher than 80° C.;
- at least one second enzyme, wherein said second enzyme is a lipase; and
- one or more monoglycerides.

In a particular embodiment the method as disclosed herein provides that said baked product shows improved short bite, preferably wherein the maximum force needed to break a baked product, prepared using at least one first enzyme being a thermophilic serine protease having an optimum activity at a temperature higher than 70° C., preferably at a temperature higher than 75° C. and preferably at a temperature higher than 80° C., and using at least one second enzyme being a lipase; is reduced with at least 15% compared to a reference baked product prepared using none of said first or second enzyme. In particular embodiments the maximum force needed to break a baked product using said first and second enzyme is reduced with at least 20% compared to a reference baked product prepared using none of said first or second enzyme. In particular embodiments the short bite is measured the day after baking.

In a particular embodiment the method as disclosed herein provides that said baked product shows improved short bite, preferably wherein the maximum force needed to break a baked product, prepared using at least one first enzyme being a thermophilic serine protease having an optimum activity at a temperature higher than 70° C., preferably at a temperature higher than 75° C. and preferably at a temperature higher than 80° C., and using at least one second enzyme being a lipase; is reduced with at least 15% compared to a reference baked product prepared using either said first or said second enzyme. In particular embodiments the maximum force needed to break a baked product using said first and second enzyme is reduced with at least 20% compared to a reference baked product prepared using either said first or said second enzyme. This shows that the combination of said first and said second enzyme provides in a synergistic action which provides in a better than expected improved short bite. In particular embodiments the short bite is measured the day after baking.

In a particular embodiment the method as disclosed herein provides that no adverse effects on dough rheology, on the crumb structure and on the volume of the resulting bakery product are observed.

Furthermore, in a further aspect, the present invention relates to a baked product prepared from a dough or batter comprising the composition as disclosed herein.

In the context of the present invention a baked product is a bakery or patisserie product known in the art, such as for instance those selected from the group comprising bread, soft rolls, bagels, donuts, Danish pastry, hamburger rolls, pizza, pita bread, ciabatta, sponge cakes, cream cakes, pound cakes, muffins, cupcakes, steamed cakes, waffles, brownies, cake donuts, yeast raised donuts, baguettes, rolls, crackers, biscuits, cookies, pie crusts, rusks and other baked products. More preferably the present invention refers to bread, baguettes and rolls. In particular said baked product is a soft bakery products and crusty bakery products, preferably bread, soft rolls, donuts, buns, microwavable buns, Danish pastry, croissants, hamburger rolls, pizza and pita bread and cake.

EXAMPLES

Example 1: Enzyme Activities Determination

The protease activity is measured on azurine crosslinked casein (AZCL-casein). It is prepared by dyeing and crosslinking casein to produce a material which hydrates in water but is water-insoluble. Hydrolysis by proteases produces water soluble dyed fragments, and the rate of release of these (increase in absorbance at 590 nm) can be related directly to enzyme activity (Protazyme AK Tablets, Megazyme, Ireland). A protazyme AK tablet is incubated in 100 mM $Na_2HPO_4.2H_2O$; pH 7.0 at 60° C. for 5 min.

An aliquot of enzyme (1.0 ml) is added and the reaction is allowed to continue for exactly 10 min. The reaction is terminated by the addition of tri-sodium phosphate (10 ml, 2% w/v, pH 12.3). The tube stands for approx. 2 min at room temperature and the content is filtered. The absorbance of the filtrate is measured at 590 nm against a substrate blank.

The activity is expressed as:

$$mU \text{ (milliunits)/ml} = (34.2*(Abs_{590} \text{ enzyme} - Abs_{590} \text{ blank}) + 0.6)/\text{dilution}.$$

One unit corresponds to 1000 mU.

The lipase activity is measured using p-nitrophenyl palmitate (pNPP) as substrate. The release of yellow p-nitrophenol due to hydrolysis of p-nitrophenyl palmitate by lipase is measured by spectrophotometry at 414 nm. One lipase milliunit (LmU) is defined as the amount of enzyme needed to release one nanomole (nmole) per minute of p-nitrophenol from p-nitrophenyol palmitate at 45° C. and pH 7.5. To perform the test, a 120 µl 1 mM pNPP solution (0.05 M Na-phosphate buffer at pH 7.5 containing 0.69 M acetone and 0.0049 M Triton X-100) is mixed with a 60 µl enzyme sample and incubated at 45° C. for 30 min.

The absorbance is measured at 414 nm against a substrate blank in 96-wells microtiter microplates.

The activity is expressed as:

$$LmU/ml = (((\text{Abs enzyme} - \text{Abs blank})/30) \times 0.18))/(13380 \times 0.06)) \times \text{sample dilution} \times 1000000$$

[30=reaction time in minutes; 0.18=reaction volume in ml; 13380=molar extinction coefficient at 414 nm ($M^{-1} cm^{-1}$); 0.06=enzyme sample volume in ml; 1000000 to convert in LmU/ml]

One lipase unit (LU) corresponds to 1000 lipase milliunits (LmU)

Example 2: Soft Buns

Soft buns were prepared using the dough compositions of Table 1. The enzymes used were the following:

TlLip: *Thermomyces lanuginosus* lipase expressed in *Aspergillus oryzae* (Noopazyme—Novozymes, Denmark).

TaProt: *Thermus aquaticus* Taq1 protease. (aqualysine I) as described in WO2009138447A1. The enzyme has an optimum of temperature activity of 80° C.

TABLE 1

| Ingredients (grams) | REF | P | L | 2P | 2L | PL | P2L | 2PL | 2P2L |
|---|---|---|---|---|---|---|---|---|---|
| Wheat Flour (Duo; Ceres; Belgium)) | 2000 | 2000 | 2000 | 2000 | 2000 | 2000 | 2000 | 2000 | 2000 |
| Water | 1100 | 1100 | 1100 | 1100 | 1100 | 1100 | 1100 | 1100 | 1100 |
| Fresh Yeast (Bruggeman, Belgium) | 60 | 60 | 60 | 60 | 60 | 60 | 60 | 60 | 60 |
| Sodium Chloride | 40 | 40 | 40 | 40 | 40 | 40 | 40 | 40 | 40 |
| Margarine Aristopan (Puratos, Belgium) | 60 | 60 | 60 | 60 | 60 | 60 | 60 | 60 | 60 |
| Sugar (sucrose) | 20 | 20 | 20 | 20 | 20 | 20 | 20 | 20 | 20 |
| Calcium propionate | 4 | 4 | 4 | 4 | 4 | 4 | 4 | 4 | 4 |
| Bread improver* | 40 | 40 | 40 | 40 | 40 | 40 | 40 | 40 | 40 |
| Enzymes | | | | | | | | | |
| TaProt (units) | | 7 | | 14 | | 7 | 7 | 14 | 14 |
| TlLip (LU) | | | 0.6 | | 1.2 | 0.6 | 1.2 | 0.6 | 1.2 |

*contains flour, mono-and diacetyl tartaric acid esters of mono- and diglycerides of fatty acids (E472e), dextrose, ascorbic acid, enzymes (alpha amylase, xylanase)

The ingredients are mixed for 2 min at low and 6 min at high speed in a spiral mixer type Diosna (SP24). The final dough temperature is 27° C. After a bulk proof of 5 min, a 1500 g dough is rounded and proofed during 10 min at bakery temperature (25° C.) and humidity (50-55%). 50 g dough pieces are made up using a Eberhardt moulder. These dough pieces are proofed at 35° C. for 85 min at 95% relative humidity in a Koma proofbox. The buns are then baked at 250° C. during 9 min in a Miwe Condo deck oven without steam. It is obvious to one skilled in the art that same end results can be obtained by using equipment of other suppliers.

The short bite of the buns was evaluated the day after baking with a TA-XT2™ texture analyser equipped with a pizza tensile rig used at a speed of 20 mm/sec. This allows the measurement of the force (maximum force needed to break the bun expressed in grams (g)). As factors such as batch of flour, ambient temperature and humidity, and time between baking and test may affect said parameters, measures are compared to a reference using the same ingredients, baked and tested in parallel. For every test, 10 buns are evaluated. The standard deviation of the measurement was 33. The confidence interval was calculated by multiplying the standard deviation with the Student's law coefficient obtained by using an α-risk value of 5% and a number of degrees of liberty equal to 5. The confidence interval was 85.

Two ingredients act synergistically if the effect of the simultaneous use of the two ingredients is bigger than the sum of the effects of the ingredients taken individually, taking into account a 95% confidence interval. In other words, there is a synergy when the effect of (x g enzyme A+y g enzyme B) is bigger than the sum of the effect of x g enzyme A and the effect of y g enzyme B.

The results of the short bite measurements with the TA-XT2™ texture analyser are listed in table 2.

TABLE 2

|  | REF | P | L | 2P | 2L | PL | P2L | 2PL | 2P2L |
|---|---|---|---|---|---|---|---|---|---|
| Force Max (g) | 867 | 811 | 825 | 727 | 784 | 647 | 624 | 594 | 580 |
| Actual reduction of force compared to REF | — | −56 | −42 | −140 | −83 | −220 | −243 | −273 | −287 |
| Theoretical reduction of force for enzyme combination | — | — | — | — | — | −98 | −139 | −182 | −223 |

The results show that the actual reduction of force obtained when enzymes are combined is lower than the lower limit of the confidence interval of the theoretical value (additive effect), demonstrating a synergistic effect on short bite.

The short bite of the buns was also evaluated the day after baking by a trained panel of bakery experts. They were asked to mark the products according to a reference on a 0 to 10 points line scale with 0 being the low end (chewy) and 10 the high end (short).

The standard deviation of the sensorial short bite measurement is 0.3. The confidence interval was calculated by multiplying the standard deviation with the Student's law coefficient using an α-risk value of 5% and a number of degrees of liberty equal to 5. The confidence interval was 0.5.

The results are listed in table 3.

TABLE 3

|  | REF | P | L | 2P | 2L | PL | P2L | 2PL | 2P2L |
|---|---|---|---|---|---|---|---|---|---|
| Short bite | 4.3 | 4.8 | 4.9 | 5.5 | 5.7 | 6.4 | 7.0 | 7.2 | 8.0 |
| Actual increase of short bite compared to REF | — | +0.5 | +0.6 | +1.2 | +1.4 | +2.1 | +2.7 | +2.9 | +3.7 |
| Theoretical increase of short bite for enzyme combination | — | — | — | — | — | +1.1 | +1.9 | +1.8 | +2.6 |

The results show that the actual increase of short bite obtained when enzymes are combined is higher than the higher limit of the confidence interval of the theoretical value (additive effect), demonstrating a synergistic effect on short bite.

Example 3a: Other Lipase (1)

Soft buns were prepared according to the recipe and the process of example 2 using the enzyme combinations listed in Table 4. The enzymes used were the following:
RmLip: *Rhizomucor miehei* lipase expressed in *Aspergillus oryzae* (Palatase 2000L—Novozymes, Denmark).
TaProt: as in example 1

TABLE 4

|  | Enzymes | | | |
|---|---|---|---|---|
|  | REF2 | LB | PB | LBPB |
| TaProt (units) |  |  | 7 | 7 |
| RmLip (LU) |  | 2.76 |  | 2.76 |

Short bite of the buns was evaluated with the same methods as in example 1. Standard deviation and confidence interval for the texture analysis were equal to 38 and 97 respectively. Standard deviation and confidence interval for the sensorial analysis were equal to 0.2 and 0.5 respectively.

Results are presented in Table 5 (texture analysis) and table 6 (sensorial analysis)

TABLE 5

|  | REF2 | LB | PB | LBPB |
|---|---|---|---|---|
| Force Max (g) | 850 | 726 | 796 | 542 |
| Actual reduction of force compared to REF2 | — | −124 | −54 | −308 |
| Theoretical reduction of force for enzyme combination | — | — | — | −178 |

TABLE 6

|  | REF2 | LB | PB | LBPB |
|---|---|---|---|---|
| Short bite (sensorial score) | 5.5 | 7.0 | 6.1 | 8.5 |
| Actual increase of short bite compared to REF2 | — | +1.5 | +0.6 | +3.0 |
| Theoretical increase of short bite for enzyme combination | — | — | — | +2.1 |

Synergistic effect of the enzymes combination is observed

Example 3b: Other Lipase (2)

Soft buns were prepared according to the recipe and the process of example 1 using the enzyme combinations listed in Table 7. The enzymes used were the following:

RoLip: *Rhizopus oryzae* lipase (Bakezyme L 80000 B-DSM)

TaProt as in example 1

TABLE 7

|  | Enzymes | | | |
|---|---|---|---|---|
|  | REF3 | LC | PC | LCPC |
| TaProt (units) |  |  | 7 | 7 |
| RoLip (LU) |  | 0.0028 |  | 0.0028 |

Short bite of the buns was evaluated with the same methods as in example 1.

Results are presented in Table 8

TABLE 8

|  | REF3 | LC | PC | LCPC |
|---|---|---|---|---|
| Force Max (g) | 850 | 738 | 796 | 655 |
| Actual reduction of force compared to REF3 | — | −112 | −54 | −195 |
| Theoretical reduction of force for enzyme combination | — | — | — | −166 |
| Short bite (sensorial score) | 5.5 | 6.8 | 6.1 | 8.0 |
| Actual increase of short bite compared to REF3 | — | +1.3 | +0.6 | +2.5 |

TABLE 8-continued

|  | REF3 | LC | PC | LCPC |
|---|---|---|---|---|
| Theoretical increase of short bite for enzyme combination | | | | +1.9 |

Synergistic effect is observed with a third lipase.

Example 4: Other Proteases

Soft buns were prepared according to the recipe and the process of example 1 using the enzyme combinations listed in Tables 9 & 10. The enzymes used were the following:

TlLip: *Thermomyces lanuginosus* lipase expressed in *Aspergillus oryzae* (Noopazyme—Novozymes).

SuProt: serine protease from *Bacillus licheniformis* (subtilisin—P5380-1G, Sigma Aldrich). The enzyme has an optimum of temperature activity of 60° C.

ThProt: metalloprotease from *Geobacillus stearothermophilus* (thermolysin—P1512-1G, Sigma Aldrich)

TABLE 9

|  | Enzymes | | | |
|---|---|---|---|---|
|  | REF4 | LD | PD | LDPD |
| TlLip (LU) |  | 0.6 |  | 0.6 |
| SuProt (units) |  |  | 10.4 | 10.4 |

TABLE 10

|  | Enzymes | | | |
|---|---|---|---|---|
|  | REF5 | LE | PE | LEPE |
| TlLip (LU) |  | 0.6 |  | 0.6 |
| ThProt (units) |  |  | 1.05 | 1.05 |

Short bite of the buns was evaluated with the texture analysis method as in example 1.

Results are presented in Table 11 and 12

TABLE 11

|  | REF4 | LD | PD | LDPD |
|---|---|---|---|---|
| Force Max (g) | 689 | 644 | 631 | 631 |
| Actual reduction of force compared to REF4 | — | −45 | −58 | −58 |
| Theoretical reduction of force for enzyme combination | — | — | — | −103 |

TABLE 12

|  | REF5 | LE | PE | LEPE |
|---|---|---|---|---|
| Force Max (g) | 654 | 588 | 591 | 559 |
| Actual reduction of force compared to REF5 | — | −66 | −63 | −95 |
| Theoretical reduction of force for enzyme combination | — | — | — | −129 |

No synergistic effect is observed with a protease having an optimum temperature activity of 65° C. and with a metalloprotease.

The invention claimed is:

1. A dough or batter comprising:
   at least one first enzyme, wherein said first enzyme is a thermophilic serine protease having an optimum activity at a temperature higher than 70° C.; and;
   at least one second enzyme, wherein said second enzyme is a triacylglycerol lipase or a triacylglycerol acylhydrolase as defined by enzyme entry EC 3.1.1.3; wherein said second enzyme is selected from lipases obtained from *Thermomyces lanuginosus, Rhizopus oryzae* and *Rhizomucor miehei* and wherein said second enzyme is added to the dough or batter:
   in an amount of 5 to 100 LU/100 kg of flour, when measured as described in Example 1, when the second enzyme is a lipase from *Thermomyces lanuginosus;*
   in an amount of 0.023 to 0.360 LU/100 kg of flour, when measured as described in Example 1, when the second enzyme is a lipase from *Rhizopus oryzae;* or
   in an amount of 50 to 200 LU/100 kg of flour, when measured as described in Example 1, when the second enzyme is a lipase from *Rhizomucor miehei.*

2. The dough or batter according to claim 1, wherein said first enzyme is a thermophilic serine protease wherein the ratio between the protease activity at optimum temperature and the protease activity at 25° C. is higher than 10 or higher than 15.

3. The dough or batter according to claim 1, wherein:
   said first enzyme is a neutral or an alkaline thermophilic serine protease; or
   said first enzyme is present in an amount of 100 to 1200 units/100 kg of flour, 200 to 900 units/100 kg of flour, or 350 to 700 units/100 kg of flour.

4. The dough or batter according to claim 1, wherein said dough or batter is a dough or batter for the preparation of soft bakery products and crusty bakery products.

5. A method for preparing a baked product, comprising the steps of adding to a dough or batter, prior to baking:
   at least one first enzyme, wherein said first enzyme is a thermophilic serine protease having an optimum activity at a temperature higher than 70° C.; and;
   at least one second enzyme, wherein said second enzyme is a triacylglycerol lipase or a triacylglycerol acylhydrolase as defined by enzyme entry EC 3.1.1.3; wherein said second enzyme is selected from lipases obtained from *Thermomyces lanuginosus, Rhizopus oryzae* and *Rhizomucor miehei* and wherein said second enzyme is added to the dough or batter:
   in an amount of 5 to 100 LU/100 kg of flour, when measured as described in Example 1, when the second enzyme is a lipase from *Thermomyces lanuginosus;*
   in an amount of 0.023 to 0.360 LU/100 kg of flour, when measured as described in Example 1, when the second enzyme is a lipase from *Rhizopus oryzae;* or
   in an amount of 50 to 200 LU/100 kg of flour, when measured as described in Example 1, when the second enzyme is a lipase from *Rhizomucor miehei.*

6. The dough or batter according to claim 1 used in the preparation of a baked product with an improved short bite, wherein the maximum force needed to break the prepared baked product is reduced with at least 15% compared to a reference baked product prepared using none of said first or second enzyme.

7. The method according to claim 5, wherein said first enzyme is a thermophilic serine protease having an optimum activity at a temperature higher than 80° C.

8. The method according to claim 5, wherein said first enzyme is a thermophilic serine protease wherein the ratio between the protease activity at optimum temperature and the protease activity at 25° C. is higher than 10.

9. The method according to claim 5, wherein said first enzyme is a thermophilic serine protease wherein the ratio between the protease activity at optimum temperature and the protease activity at 25° C. is higher than 15.

10. The method according to claim 5, wherein said first enzyme is a neutral or an alkaline thermophilic serine protease.

11. The method according to claim 5, wherein said first enzyme is a Taq protease.

12. The method according to claim 5, wherein said first enzyme is a Taq protease isolated from *Thermus aquaticus.*

13. The method according to claim 5, wherein said first enzyme is aqualysin I or aqualysin II.

14. The method according to claim 5, wherein said first enzyme is aqualysin I isolated from *Thermus aquaticus* LMG8924.

15. The method according to claim 5, wherein said first enzyme is added to the dough or batter in an amount of 100 to 1200 units/100 kg of flour.

16. The method according to claim 5, wherein said baked product shows improved short bite, wherein the reduction in the maximum force needed to break the baked product prepared using the combination of the at least one first enzyme and the at least second enzyme is greater than the sum of the reduction in the maximum force needed to break a baked product prepared with the at least one first enzyme, and the reduction in the maximum force needed to break a baked product prepared with the at least second enzyme, taken individually.

17. The method according to claim 5, wherein no adverse effects on dough rheology, on crumb structure and on loaf volume of the baked product are observed, wherein the baked product is prepared from a dough or batter comprising the at least one first enzyme and the at least one second enzyme, wherein the baked product is compared to a reference baked product, and wherein the reference baked product is prepared with said first enzyme or wherein the reference baked product is a baked product prepared with said second enzyme alone.

18. The method according to claim 5, wherein a maximum force needed to break the baked product, prepared using the at least one first enzyme and the at least second enzyme, is reduced by at least 15% compared to a reference baked product, wherein the reference baked product is prepared using none of said first or second enzyme.

19. The method according to claim 5, wherein said second enzyme is added to the dough or batter:
   in an amount of 20 to 60 LU/100 kg of flour, when measured as described in Example 1, when the second enzyme is a lipase from *Thermomyces lanuginosus;*
   in an amount of 0.09 to 0.18 LU/100 kg of flour, when measured as described in Example 1, when the second enzyme is a lipase from *Rhizopus oryzae;* or
   in an amount of 90 to 160 LU/100 kg of flour, when measured as described in Example 1, when the second enzyme is a lipase from *Rhizomucor miehei.*

20. A baked product prepared from the dough or batter according to claim 1.

* * * * *